United States Patent [19]

Larson et al.

[11] Patent Number: 5,315,113
[45] Date of Patent: May 24, 1994

[54] SCANNING AND HIGH RESOLUTION X-RAY PHOTOELECTRON SPECTROSCOPY AND IMAGING

[75] Inventors: Paul E. Larson, Bloomington; Paul W. Palmberg, Edina, both of Minn.

[73] Assignee: The Perkin-Elmer Corporation, Conn.

[21] Appl. No.: 953,429

[22] Filed: Sep. 29, 1992

[51] Int. Cl.$^5$ .............................................. H01J 49/48
[52] U.S. Cl. .................................... 250/305; 250/306; 378/84; 378/85
[58] Field of Search ............... 250/305, 306, 307, 310; 378/84, 85

[56] References Cited

U.S. PATENT DOCUMENTS

| Re. 33,275 | 7/1990 | Wardell et al. | 250/305 |
|---|---|---|---|
| 3,567,926 | 3/1971 | Siegbahn | 250/49.3 |
| 3,617,741 | 11/1971 | Siegbahn et al. | 250/49.5 |
| 3,766,381 | 10/1973 | Watson | 250/49.5 |
| 3,772,522 | 11/1973 | Hammond et al. | 250/503 |
| 3,810,879 | 3/1989 | Walker | 250/305 |
| 4,048,498 | 9/1977 | Gerlach et al. | 250/305 |
| 4,680,467 | 7/1987 | Bryson, III et al. | 250/305 |
| 4,752,685 | 6/1988 | Shiokawa et al. | 250/305 |
| 4,810,880 | 3/1989 | Gerlach | 250/305 |
| 5,118,941 | 6/1992 | Larson | 250/310 |
| 5,127,028 | 6/1992 | Wittry | 378/84 |

OTHER PUBLICATIONS

"A Wide-Angle Secondary Ion Probe for Organic Ion Imaging" by C. C. Grimm, R. T. Short, and P. J. Todd, J. Am. Soc. Mass Spectrum 1991, 2, 362-371.

"AXIS: An Imaging X-Ray Photoelectron Spectrometer" by I. W. Drummond, F. J. Street,, L. P. Ogden, and D. J. Surman, Scanning 13, 149-163 (Mar.-Apr. 1991).

*Primary Examiner*—Paul M. Dzierzynski
*Assistant Examiner*—Kiet T. Nguyen
*Attorney, Agent, or Firm*—H. S. Ingham; E. T. Grimes

[57] ABSTRACT

An instrument for surface analysis includes a gun for selectively focusing an electron beam on an anode spot, or rastering the beam across an array of such spots, to generate x-rays. A concave monochromator focuses an energy peak of the x-rays to a specimen surface, in a spot on a selected pixel area or across an array of pixel areas on the surface to emit photoelectrons. An analyzer with a detector provides information on the photoelectrons and thereby chemical species in the surface. A second detector of low energy photoelectrons is cooperative with the rastering to produce a scanning photoelectron image of the surface, for viewing of a specimen to be positioned, or for imaging an insulator surface. The monochromator is formed of platelets produced by cutting an array of platelets from a single crystal member, and bonding the platelets to a concave face of a base plate juxtaposed in crystalline alignment in a positioned array identical to that of the initial array.

34 Claims, 4 Drawing Sheets

SCANNING AND HIGH RESOLUTION X-RAY PHOTOELECTRON SPECTROSCOPY AND IMAGING

This invention relates generally to electron microanalysis of surfaces, and particularly to high-resolution x-ray scanning photoelectron spectroscopy and imaging.

BACKGROUND OF THE INVENTION

A variety of electron microscopes and associated surface analyzers have evolved in recent years. One approach to chemometric surface analysis is electron spectroscopy for chemical analysis (ESCA) which involves irradiating a sample surface with ultraviolet or preferably x-rays and detecting the characteristic photoelectrons emitted. The latter method is also known as x-ray photoelectron spectroscopy (XPS). The photoelectrons are filtered by an electrostatic or magnetic analyzer which allow only electrons of a specified narrow energy band to pass through to a detector. The intensity of the detected beam typically represents the concentration of a given chemical constituent on or near a specimen surface. U.S. Pat. No. 3,766,381 (Watson) describes such a system, including an electrostatic hemispherical type of analyzer.

Another method for analyzing surfaces utilizes secondary Auger electrons generated at a small area of sample surface by a focused primary electron beam. Surface mapping of elements is accomplished by scanning with the primary electron beam. An example of a scanning Auger microprobe utilizing a cylindrical type of electrostatic electron analyzer is provided in U.S. Pat. No. 4,048,498 (Gerlach et al).

A more commonly known instrument is a scanning electron microscope (SEM) in which a focused electron beam is rastered over a surface. Secondary electrons emitted from the surface are detected in correlation with rastering positions. The secondary electron signals are processed electronically to provide a picture or image of topographical features of the surface. An SEM itself does not provide chemometric analysis. Another limitation of the SEM is imaging the surface of some insulators, because of rapid charge buildup from the incident beam of electrons. Conductive coatings or other techniques are used to alleviate charging, but at the loss of surface details, time and cost of extra preparation, and loss of ability to remove surface layers during analysis. U.S. Pat. No. 5,118,941 (Larson) discloses that insulator specimens can be imaged with a single frame of SEM rastering, but at the expense of resolution.

The latter patent also discloses a system for locating target area for microanalysis of a specimen surface, using an SEM in conjunction with the microanalyzer. Backscattered electrons from the SEM electron beam are passed through the analyzer for producing a further image that is superimposed on the SEM image, such that the further image represents the target area for microanalysis.

Thus systems involving electron beam impingement on a specimen surface have evolved into high sensitivity instruments, in which very small areas may be selected for analysis. Rastering can be used to provide images or chemical mapping of the surface. However, similar small-area sensitivity and raster mapping has been elusive for x-ray photoelectron spectroscopy (XPS).

X-rays from an anode target have been focused onto the specimen by means of a concave crystal monochrometer, as taught in U.S. Pat. Nos. 3,567,926 (Siegbahn) and 3,617,741 (Siegbahn et al).

A method of construction of a concave monochrometer for focusing x-rays is disclosed in U.S. Pat. No. 3,772,522 (Hammond et al), in which a quartz crystal disk is brazed with a metal film onto a concave spherical surface of a substrate. Because of a tendency of the disk to break during mounting to the curvature, a number of platelets may be bonded to the surface, for example in a monochrometer used in a PHI model 5600 instrument sold by Perkin-Elmer. Bonding techniques include brazing, optical contacting, epoxy and the like. The platelets are cut sequentially from the end of a single crystal rod of quartz.

A second approach to reduced area analysis has been to use an x-ray beam that floods the specimen surface, combined with a small-area objective lens for the photoelectrons, such as taught in U.S. Pat. No. Re. 33,275 (Wardell et al) for an electrostatic objective lens. Direct XPS imaging of a surface flooded with x-rays, using a type of magnetic lens variously known as an immersion lens, single pole piece lens or snorkel lens, is taught in U.S. Pat. Nos. 4,810,880 (Gerlach) and 4,810,879 (Walker).

Scanning for XPS may be effected by rastering the sample or the lens mechanically, which is cumbersome. Scanning is also achieved by electronic deflection in the objective lens to receive electrons from off-axis, in a manner as described in an article "A Wide-angle Secondary Ion Probe for Organic Ion Imaging" by C.C. Grimm, R.T. Short, and P.J. Todd, J. Am Soc. Mass. Spectrum 1991, 2, 362-371. Such scanning for photoelectrons is disclosed in an article "AXIS: An Imaging X-Ray Photoelectron Spectrometer" by I.W. Drummond, F.J. Street, L.P. Ogden, and D.J. Surman, SCANNING 13, 149-163 (March-April 1991).

A more precision type of x-ray microscope utilizes zone plates and mirror techniques. This requires a very intense source of x-rays such as from a synchrotron, and so is not practical for general use.

SUMMARY OF THE INVENTION

One aspect of the present invention is an improved instrument for chemometric surface analysis of a selected pixel area on a specimen surface by x-ray photoelectron analysis providing improved sensitivity. Another aspect is a novel instrument for chemometric mapping across a surface area by x-ray photoelectron analysis. A further aspect is sensitive imaging of a sample surface from photoelectrons generated by focused x-rays. Yet another aspect is an x-ray monochromator for providing improved sensitivity and precision in such instruments. Another aspect is improved chemometric analysis and imaging of insulator surfaces.

The foregoing and other aspects are achieved with an instrument for analysis of a specimen surface, the instrument including an electron gun for producing a focused electron beam, and an anode with a surface disposed to receive the focused electron beam so as to generate x-rays. A directing means selectively directs the focused electron beam onto a selected anode spot on the anode surface, whereby the x-rays are generated from the selected anode spot. A focusing means is receptive of the x-rays for focusing a narrow energy band of x-rays in an x-ray spot on a selected pixel area of a specimen surface, such that photoelectrons are emitted from the selected pixel area.

The anode spot is selectable from an array of anode spots on the anode surface. The selected pixel area corresponds to the selected anode spot and thereby is selectable from an array of pixel areas corresponding to the array of anode spots. A detection means is receptive of photoelectrons from the selected pixel area for producing signals representative of the photoelectrons. A display means including a processor is receptive of the signals for displaying specimen information associated with the photoelectrons.

In a further aspect, the instrument includes an electron beam gun for producing a focused electron beam with an anode surface disposed to receive the focused electron beam so as to generate x-rays, and also includes rastering means for rastering the focused beam over an array of anode spots on the anode surface, whereby the x-rays are generated sequentially from each of the anode spots. A focusing means is receptive of the x-rays for focusing a narrow energy band of x-rays as an x-ray spot on a specimen surface. The rastering on the anode thereby effects movement of the x-ray spot over an array of pixel areas on the specimen surface, such that photoelectrons are emitted sequentially from each pixel area with electron energies characteristic of chemical species in such each pixel area. Thus the array of pixel areas corresponds to the array of anode spots. An analyzer with a detector is receptive of photoelectrons from the array of pixel areas for analyzing the electron energies. A processor is cooperative with the analyzer for displaying a mapping of specimen information representative of the electron energies, and thereby a mapping of the chemical species in the array of pixel areas.

In a preferred embodiment the analyzer comprises a deflector, for example a hemispherical analyzer, to deflect photoelectrons in a predetermined path for selective detection according to selected electron energy. A voltage (or other signal) is applied to the deflector to determine the selected energy. The x-ray band may have a natural x-ray energy shift across the specimen surface, in which case the deflector voltage is coordinated with the rastering means to correspondingly modulate the deflector voltage to compensate for the shift.

The instrument may additionally, or alternatively, include a detector of low energy photoelectrons directly from the specimen surface for generating corresponding signals. A processor is receptive of the signals and cooperative with the rastering means so as to produce a scanning photoelectron image of the surface. This imaging is useful for imaging of insulators, as there is no direct impingement of electrons to cause charge buildup. Loss of electrons from the insulating specimen may be neutralized by low energy flooding of electrons to the specimen surface.

A particularly precise concave monochromator is useful for focussing a selected band of x-rays in such an instrument. A base plate has a polished face with a concave curvature. A monochromator crystal arrangement comprises a plurality of crystal platelets having a uniform thickness, the platelets originating from an initial array of juxtaposed sections delineated on a flat surface of a single crystal member. The sections are cut from the crystal member to form the platelets. The polished side of the platelets are bonded to the polished face of the base member in a positioned array identical to that of the initial array, such that the platelets form the precision monochromator.

DETAILED DESCRIPTION OF THE INVENTION

Figure 1:
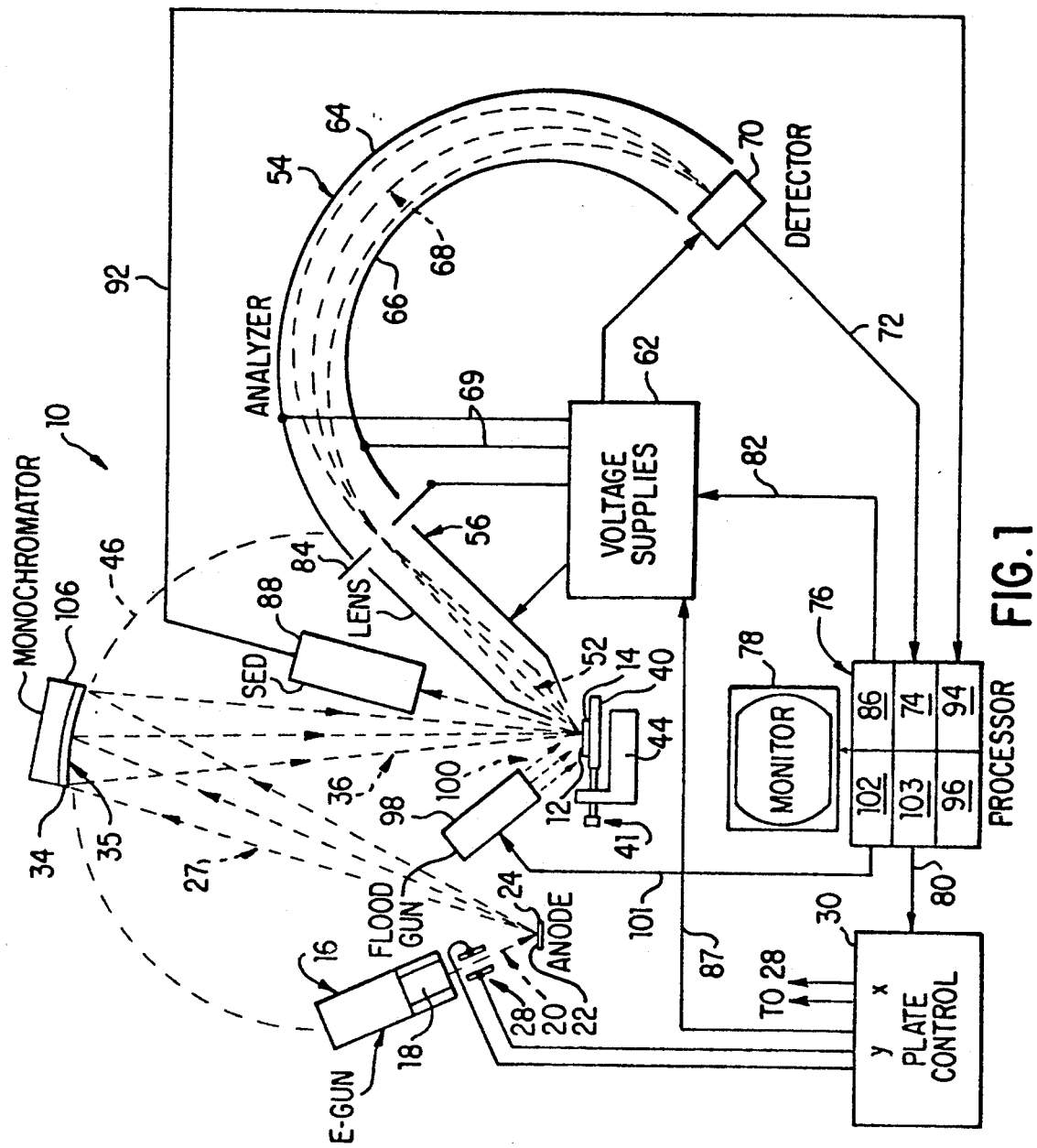
FIG. 1 is a schematic diagram of an instrument incorporating the invention.

An instrument 10 for analysis of a surface 12 of a sample specimen 14 is illustrated schematically in FIG. 1. An electron gun 16 has an appropriate electron lens system 18 for focusing an electron beam 20 onto the surface 22 of a target anode 24. The gun may be a conventional type, modified to optimize for higher power and larger beam size. The gun beam 20 should focus to a selected spot 26 (FIG. 3) on the anode surface, the spot being as small as practical, e.g. down to about 4 microns. This results in the generation of x-rays 27 from the anode, and in particular from the selected anode spot.

Figure 2:
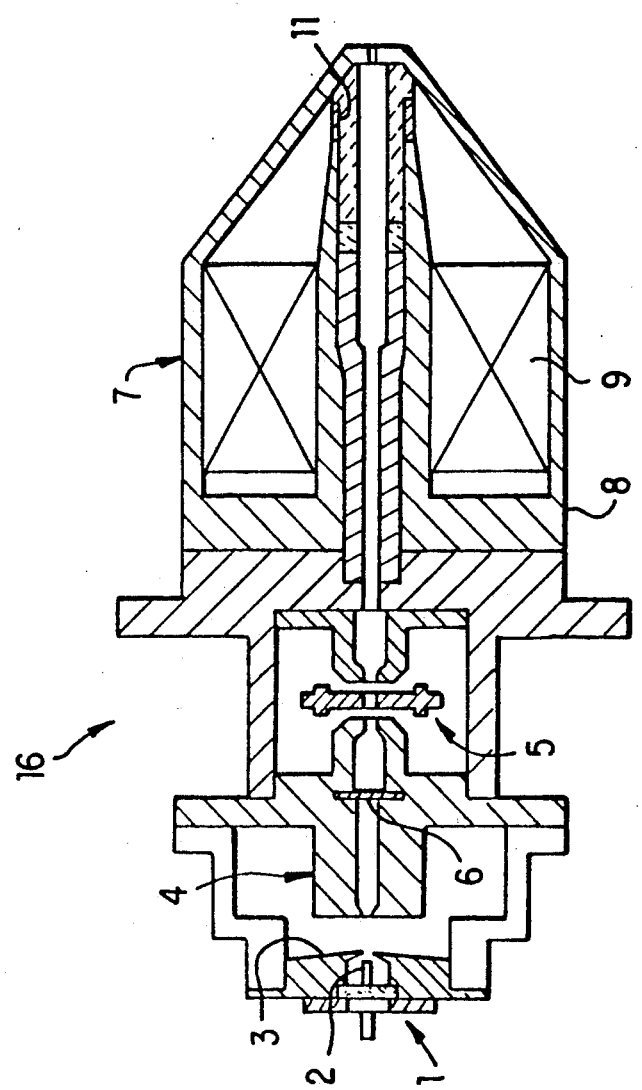
FIG. 2 is a longitudinal section of an electron gun used in the instrument of FIG. 1.

FIG. 2 illustrates a useful electron gun 16. At the rear is a Cathode assembly 1 with a LaB$_6$ cathode 2, a wenwelt 3 and an gun anode 4. The mid portion includes an electrostatic condenser lens 5 with a condenser aperture 6. A magnetic objective lens 7 includes a polepiece 8 and a coil 9. Deflection of the beam is effected with an electrostatic deflector 11. The gun is operated at 20 KV over 1 to 60 watts with a selectable beam size of 4 to 50 microns.

The target anode 24 may be formed of any metal such as aluminum that provides a desired x-ray emission energy band; ordinarily the band is substantially a line of small energy width. Preferably the target anode is at or near ground potential, and the gun cathode is operated at a negative voltage, for example − 20 KV, with respect to the anode to effect generation of x-rays including the desired band of x-rays of predetermined energy. Advantageously the selected energy band is the aluminum K-alpha line at 1.4866 KeV.

Deflection plates 28 (one pair shown in FIG. 1) selectively direct or aim the electron beam 20 from the electron gun 16 to the anode spot 26 which is selected out of an array of such spots 32 on the anode surface 22. Voltages from a deflection plate control 30, controlled by a processor 76 via line 80, are applied to the deflector plates, which are arranged in both x and y axes, to establish the amount of deflection of the beam, and thereby the selected position of the spot which may be held stationary. In an alternative aspect, the control 30 provides rastering of the focused electron beam 20 across the flat surface of the anode, i.e. over the array of anode spots 32 across the anode surface, and the x-rays 27 are emitted sequentially from successive anode spots. Typical raster speed is 100 Hz in the dispersive direction and 10 KHz in the non-dispersive direction.

A Bragg crystal monochromator 34, advantageously single-crystal quartz, is disposed to receive a portion of the x-rays 27 from the anode 24. The monochromator has a crystallographic orientation and a concave configuration 35 to select and focus a beam of x-rays 36 in the desired energy band, e.g. the K-alpha line, as an x-ray spot 38 on the specimen surface 12 to be analyzed. The x-ray spot is an image of the anode spot 26 on the specimen surface. The specimen 14 rests on a stage 40 advantageously having orthogonal micrometer positioners 42 for manual or motorized positioning with respect to a support 44 in the instrument.

Although a Bragg crystal monochromator is preferred, other focussing means may be suitable. These include grazing incidence mirrors, Fresnel zone plates and synthetic multilayer devices of alternating high and low density material (e.g. tungsten and carbon). In each case the reflector is curved to focus the diffracted x-rays onto the specimen in the manner disclosed herein.

A suitable arrangement is based on the conventional Rowland circle 46, in which the anode surface 22, the crystal 34 and the sample surface 12 are substantially on the circle, for example as taught in the aforementioned U.S. Pat. No. 3,772,522. In the plane of the drawing, the crystal has a radius of curvature equal to the diameter of the Rowland circle. For point focussing, the out-of-plane radius of curvature is $(2R \cos^2 B)$ where R is the circle radius and B is the Bragg angle. For example, the respective radii are 50 and 48 cm for 100 quartz and aluminum K-alpha x-rays and a Rowland circle radius of 25 cm. These are curvatures of the crystal lattice, not ground-in curvatures on the surface. For optimal point-to-point focussing, the crystals actually should be ellipsoidal.

The focusing of the energy band of x-rays 36 effects the x-ray spot 38 on a selected pixel area 48 of the specimen surface 12. This pixel area, which coincides with the x-ray spot, is an x-ray image of the anode spot 26. Pixel 48 is selected out of an array of such pixel areas 50 corresponding to the array of anode spots 32. The selected pixel area thereby corresponds to the selected anode spot, the location of which is determined by selection of voltages on the deflection plates 28 for the electron beam 20. Thus the position of the pixel area is effectively selected via these deflection voltages. In the case of rastering, the selected anode spot is continually changing, being each sequential spot in the array on the anode surface. The rastering of the focused beam over the array of anode spots is such that the x-ray spot is correspondingly rastered over the array of pixel areas 50 covering a desired surface area of the specimen surface.

The x-rays 36 cause photoelectrons 52 to be emitted from the selected active pixel area 48 of the specimen. The electron energies generally include a low energy peak in the range of up to 10 ev, usually about 2 to 5 ev, plus higher kinetic energy peaks or lines characteristic of chemical species (viz. chemical elements and/or their electron bondings) in the selected pixel area. In the case of rastering, the characteristic photoelectrons vary with any varying chemistry across the array of pixel areas, and the low energy electrons (commonly known as "secondary electrons") vary with topography as well. Detection or analysis of the photoelectrons is used to provide information on the surface at a selected pixel area or across the rastered array of areas. There also may be Auger electrons which, for the present purpose, are included in the term "photoelectrons" as they are caused by the x-rays.

The pixel areas on the specimen surface may be overlapped by rapid sequential processing of the analyzer signals. Very high scanning speeds for the electron beam may be desirable, for example to allow increased power and heating by reducing dwell time. Scanning speed may be between zero (for a selected spot) and 100 m/sec, for example 10 m/sec. Time per pixel may be about one microsecond, with the mapping and imaging being built up from thousands of frames.

In one embodiment of the invention (FIG. 1) an electron energy analyzer 54 receives a portion of the photoelectrons 52. The analyzer may be a known or desired type, generally either magnetic or electrostatic, which deflects the photoelectrons in a predetermined path 68 according to electron energy and thence to a detector 70. A selected control, generally an electrical signal (current or voltage), is applied to the deflector to establish the amount of deflection and so is representative of selected energy of photoelectrons deflected in the predetermined path. In a magnetic analyzer such as a magnetic prism, a current signal through the magnet coils is appropriately selected, and in a electrostatic analyzer a deflecting voltage signal is selected.

One useful type of electrostatic energy analyzer is a cylindrical type described in the aforementioned U.S. Pat. No. 4,048,498. In a preferable alternative, as shown in FIG. 1, the analyzer 54 is a hemispherical type as described in the aforementioned U.S. Pat. No. 3,766,381. The analyzing means also includes a lens system 56 such as an electrostatic lens for the input to the analyzer. The lens may combine objective and retarding functions to collect photoelectrons emitted from the effective pixel area and direct them into the analyzer in the desired kinetic energy range.

The electrostatic lens 56 may be conventional, for example a PHI Omnifocus IV TM lens of Perkin-Elmer. The lens should include pairs of orthogonal deflection plates 59 with applied voltages from a source 55. The voltages are selected, varied or oscillated via the processor 76 in cooperative synchronization with positioning or rastering of the primary electron beam 20, under control of the processor, to centralize off-axis photoelectrons so that a substantial portion of the electrons reach the slit 84 and enter into the analyzer 54.

Figure 4:
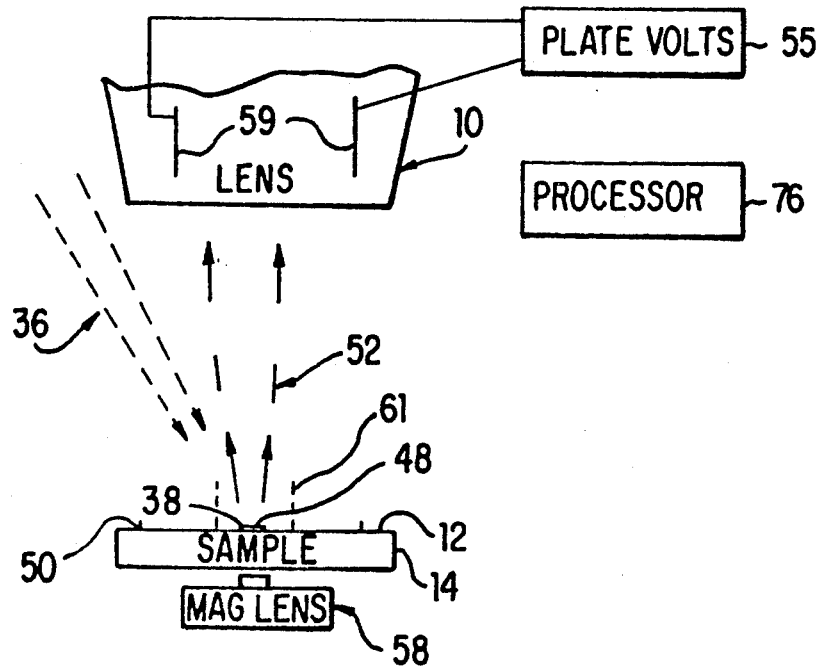
FIG. 4 is an elevation of an alternative embodiment for a magnetic lens for the instrument of FIG. 1.

An alternative for the objective lens function is a magnetic lens 58 (FIG. 4), advantageously of a type variously known as an immersion lens, a single pole piece lens or a snorkel lens as described in the aforementioned U.S. Pat. No. 4,810,880. This objective lens is situated below the specimen so that the magnetic field of the lens collects a substantial portion of the emitted photoelectrons 52 from the sample surface. To achieve this, the sample is placed proximate the immersion lens, the sample being interposed between the immersion lens and a separate electrostatic lens 60; in this case lenses 58 and 60 form the lens system 56 (FIG. 1). More generally, the sample is located between the immersion lens and the analyzer. The magnetic lens may have a collection zone (illustratively delineated by broken lines 61) of collecting electrons emitting from a portion of specimen surface being rastered. Off-center emissions may be centered by the deflector plates 59 as described above. Particularly good collection efficiency and sensitivity are attained with such a system.

Figure 3:
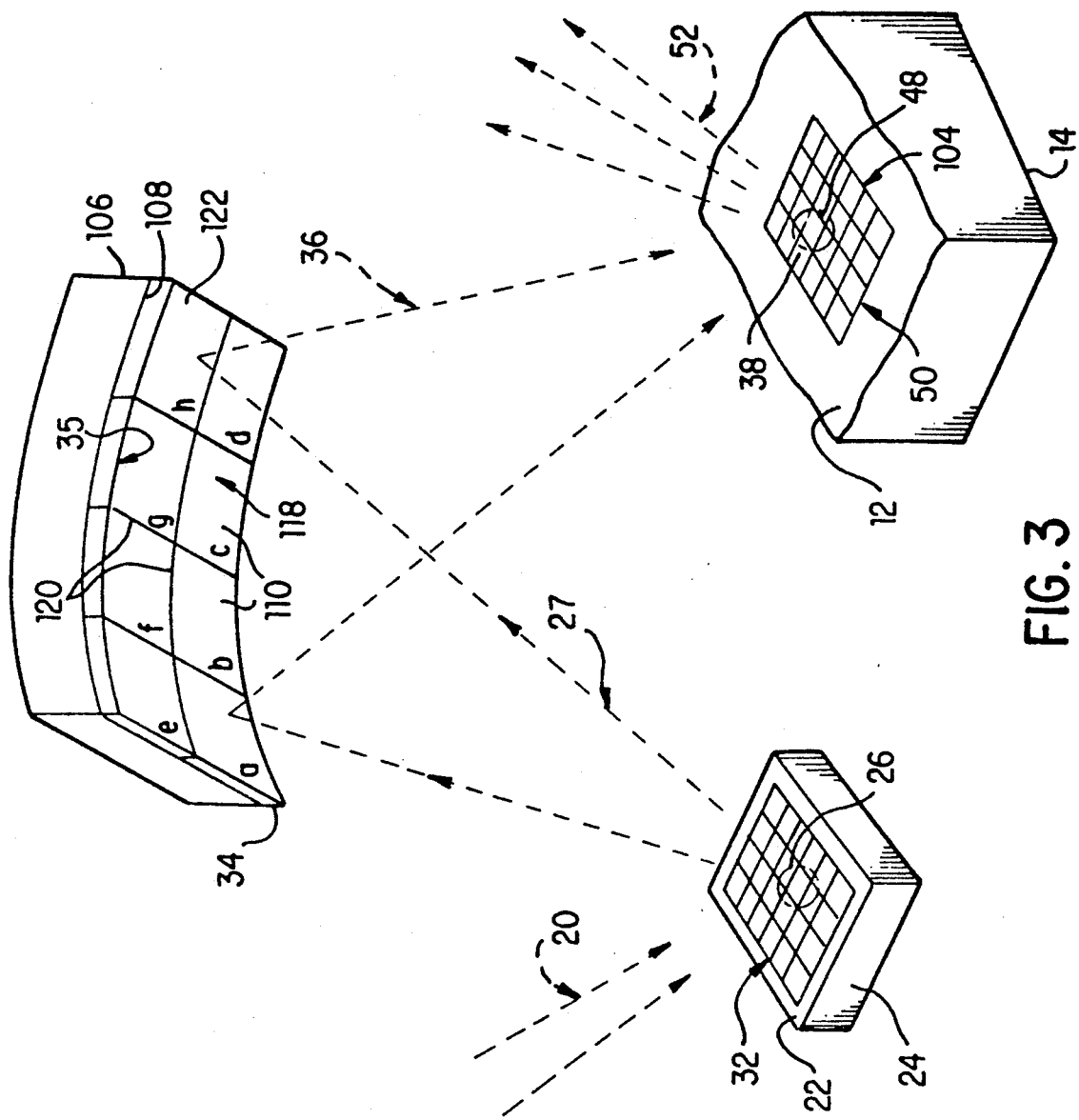
FIG. 3 is a detail in perspective of an anode, a specimen and a monochromator in the instrument of FIG. 1.

Returning to FIG. 1, with a selected voltage from a voltage source 62 applied via lines 69 across the hemispheres 64,66 of the analyzer, electrons of selected energy travel in a narrow range of trajectories 68 so as to exit the analyzer into the detector 70. The latter may be a conventional multichannel detector, for example having 16 channels for detecting a small range of electron energies passed by the analyzer in slightly different trajectories. A further lens (not shown) may be placed between the analyzer and the detector, if desired or required for certain types of detectors. Signals from the detector 70 corresponding to intensity of electron input are carried on a line or lines 72 (via an appropriate amplifier, not shown) to an analyzing portion 74 of the processing unit 76 which combines control electronics and computer processing, such as with a Hewlett Packard Model 425e computer. The processing provides electron energy information and thereby information on chemical species that are present and emitting the electrons from the particular specimen pixel area 48 (FIG. 3). The information is stored, displayed on a monitor 78, and/or printed out in the form of images, numbers and/or graphs. By cooperating the display means (which herein includes the processor) With the electron beam directing means 28,30, via line 80 from the processor to the controller 30, a mapping of the chemical species in the selected or scanned surface area is effected and displayed. The mapping provides specimen surface information corresponding to the selected pixel area location, or the rastered array of pixel areas on the specimen surface.

As indicated above, the electrostatic analyzer has a voltage applied to its capacitive elements, viz. hemispheres, that is chosen by input on line 82 from the processor 76 to determine the energy of the electrons passed through and detected. The voltage is basically DC but may be set according to selected photoelectron energy lines to be detected corresponding to chemical species in the specimen surface. Other voltages to the analyzer system are obtained from the voltage supply unit to the input lens 56, analyzer slit 84 and detector 70, in the conventional manner.

A complication arises because scanning the electron beam in the dispersive direction (parallel to the anode surface in the plane of the incident beam and emitted x-rays, i.e. in the plane of FIG. 1) causes a small shift in the emitted x-ray energy and hence the kinetic energy of the photoelectron lines. Moreover, the scanning range may be limited by the width of the desired energy band, e.g. the aluminum K-alpha line, so that the intensity will also be shifted by the line shape. Means for compensating for such shifts may be effected in several ways.

One way is to raster (oscillate) the sample instead of the electron beam. In another way the electron beam is rastered over the anode and the data is acquired with an energy analyzer (such as the spherical analyzer of FIG. 1) with an energy window wide enough to capture the shifting spectral features; software is designed to shift the spectra to a constant energy. In yet another way the geometry of the analyzer is such that the dispersion of the monochromator is compensated, as taught in the aforementioned U.S. Pat. No. 3,567,926. Or the orientation of the monochromator may be synchronously modulated so that the x-ray energy stays constant and the intensity is always maximized at the x-ray line peak. In any of the these techniques for compensation, some association with the analyzer is needed so as to coordinate the compensation with the energy-selection characteristic of the analyzer.

Another way of compensating is to have a section 86 of the processor 76 vary the energy control signal from the voltage controller 62 to the analyzer 64 synchronously with the scanning of the electron beam. For example with an electrostatic analyzer the voltage is modulated on the analyzer components 64,66,84 synchronously with the scanning of the electron beam in such a way that acquisition is constant in energy. This may be effected with software (or firmware) in the processor. The software is readily assembled theoretically or from empirical determinations of voltage changes necessary to maintain full detection of a selected energy peak for electrons 52 from the specimen 14 as the beam 20 is scanned slowly over the anode 24. Thus the processor 76 may be programmed to coordinate the signal supply 62 with the rastering means 28,30 to correspondingly Vary the voltage (or current) signal on lines 69 to the analyzer to compensate for the variation.

A simple way of coordinating the analyzer voltage to compensate is to tap a portion of the raster voltage from the deflector plates 28. Such portion is added via lines 87 to modulate the voltage on lines 69 to the analyzer hemispheres. The modulation is selected to provide the compensation.

In another embodiment of the invention the instrument 10 includes a second detector 88 that is receptive of photoelectrons 90 directly from the pixel, specifically the low energy elections of about up to 10 ev, without filtering by an analyzer. This detector then generates corresponding photoelectron signals. A further portion 94 of the processor 76 is receptive of these signals via line 92 and is cooperative with the rastering means 28,30 so as to produce a scanning photoelectron image of the surface. The image is essentially a picture of the surface, viz. a topographical picture presented on the monitor 78.

The second detector 88, denoted herein as a secondary electron detector (SED) is of the conventional type ordinarily used for scanning electron microscopes (SEM). A suitable detector is a Perkin-Elmer Model 04-202 detector, with an appropriate amplifier and (if necessary) an analog-digital converter. The resulting SED image is quite similar to that of an SEM operation, except that the detected electrons are generated by x-rays as described herein.

The SED image is particularly useful for locating an area on the specimen surface to be analyzed for chemical species by the energy analyzing embodiment. For example the image may be viewed on the screen while the specimen is moved with the stage 40. Since the image and analysis are effected from the same focus of x-rays, the locations are substantially identical for both.

The present method of imaging with the SED is useful for insulators such as aluminum oxide, since there is no electron beam impinging directly on the sample to cause build-up. However, special precautions may be required. The photoelectron emission will cause a depletion of electrons in the insulator surface, thus charging the specimen with a positive voltage which will impede further emission. To solve this in the case of rastering to analyze and map a surface according to chemical species, the instrument further has an electron gun 98 known as a flood gun that continuously floods the specimen surface 12 with a low level of electrons 100 at up to 10 ev and one microampere so as to neutralize the loss of photoelectrons from the specimen surface during rastering. Such a gun may be a PHI model 04-090 electron gun of Perkin-Elmer, or the like.

For full area spectral analysis, rastered data from all pixels are added to obtain an average spectral analysis of the entire rastered area of an insulator.

In rastering an insulator for an SED image, the instrument should further comprise pause means 102 in the programming for periodically pausing the imaging. The flood gun 98 is then operated during each pause under direction of the processor portion 102 via line 101 to irradiate the specimen surface 12 with a low level pulse (generally 0.1 to 10 microamperes) of electrons 100 at about one microampere so as to neutralize loss of photoelectrons from the surface during rastering.

Pause/pulses are necessary because detection of the low-energy flood electrons otherwise would hide or distort the image. The pause/pulses may be of 10 millisecond duration at 100 millisecond intervals. However, the flood gun can be operated continuously during spectral acquisitions.

Differential charging effects may occur at the edges of a rastered area of an insulator where full-area analysis is being performed. To account for this, the processor may include means 103 such as software for blocking peripheral pixel areas 104 (FIG. 3) of the array of pixel areas from the spectral data.

For clarity the several functional portions of the processor 76 are shown separately in FIG. 1. However such portions actually may include a commonality of components and various sections of a computer program. Any computer programs mentioned or implied herein are readily prepared in a conventional language such as "C" generally available from the supplier of the computer used. Some portions of the programming may be embedded in PROM chips as firmware.

Analysis of a small selected pixel area 48 (FIG. 3) on a specimen, or of a plurality of such areas 50 in a scanning mode, is advantageously effected with a very small anode spot 26 combined with a precision monochromator 34 to focus a similarly small spot 38 of the selected energy band of x-rays on the specimen. As indicated above, the monochromator crystal is oriented crystallographically to effect the selected x-ray band, and is curved for the focusing. For example a quartz crystal will be oriented (prior to curvature) in a 100 plane (also known as a 1,0,0 plane or a y-axis plane or a "zero degree y cut"). The monochromator is advantageously mounted on a base member 106 having a polished face 108 with the desired concave curvature, as a thin crystal 34 bonded to the face so as to assume the curvature. The base plate should be of the same or similar material to match thermal expansion coefficients; glass is a suitable base for quartz crystal.

To facilitate construction the monochromator crystal 34 advantageously comprises a plurality of crystal platelets 110 having a uniform thickness. The platelets are formed of common (same) material, lattice structure, and crystalline orientation with respect to a polished surface of the platelets bonded to the base member. The crystal platelets are bonded to the face 108 juxtaposed like tiles in crystalline alignment so as to assume the concave curvature. The bonding may be by conventional means but should introduce as little imperfection to the interface as possible.

Figure 5:
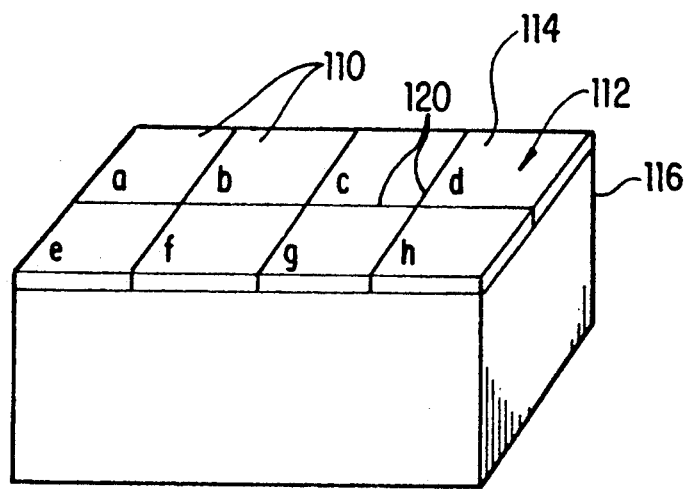
FIG. 5 is a perspective of a crystal member used for forming the monochromator of FIG. 3.

According to a preferred embodiment (FIG. 5) the platelets 110 are produced by delineating an initial array 112 of juxtaposed sections from a planar surface 114 of a single crystal member 116 and cutting the delineated sections from the member. Alternatively the single crystal may be cut initially to the desired thickness of the platelets, before delineating and cutting the platelets. Polished sides of the platelets are then bonded to the polished face 108 in a positioned array 118 (FIG. 3) with crystallographic alignment identical to that of the initial array 112. The initial and positioned arrays are illustrated by the lettering a through h respectively in FIGS. 5 and 3. This origination of platelets ensures that the platelets are formed of common material, lattice structure and crystalline orientation.

To produce a monochromator of high precision, the following procedure is advantageous: A 40 by 40 mm quartz crystal 5 to 10 mm thick is prepared with a large face oriented zero degrees to the y-axis. The crystal should be thick enough for rigidity during subsequent polishing and thinning but not so thick as to unduly encumber the subsequent thinning process. The crystal is examined interferometrically and rejected if twinned. The large face is lapped and polished optically flat, preferably within one-tenth wave per inch (0.04 wave/cm) at a wavelength of 632.8 nm. This polished face is x-rayed near the center and each corner to establish that the orientation at each point is exactly the same, and the mean is within one arc-minute of the y-axis. The platelets are contacted to an optically flat support member, e.g. within one-tenth wave per inch (0.04 wave/cm), retaining the same juxtaposition of relative locations (including rotation) with crystallographic alignment as in the original crystal. The platelets are thinned to a final predetermined thickness between 50 and 100 microns (uniform preferably within +/−5 microns) and polished so the faces are parallel within one-tenth wave per inch (0.04 wave/cm) over the entire 40 by 40 mm. The platelets are removed from the support member and bonded to the polished face of the base member in the same relative locations (including rotation) as in the original crystal.

Numbers of platelets ranging from 4 to 16 in a total area of 40 by 40 mm may be suitable. Each side dimension is advantageously in the the range of 10 to 20 mm. The sensitivity of the monochromator is substantially proportional to the solid angle of radiation intercepted as viewed from the anode, approximately according to the formula: (crystal area)/(Rowland circle diameter)$^2$. Larger solid angles improve sensitivity but introduce aberrations limiting both energy and spacial resolution. For the dimensions given herein, the solid angle is 0.04 steradians. Such a monochromator can provide an x-ray spot on the specimen that is substantially the same size as the electron beam on the anode, subject only to monochromator broadening of about 10 microns.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

We claim:

1. An instrument for analysis of a specimen surface, comprising:

an electron gun for producing a focused electron beam;

an anode with an anode surface disposed to receive the focused electron beam so as to generate x-rays;

directing means for selectively directing the focused electron beam to a selected anode spot on the anode surface whereby the x-rays are generated from the selected anode spot, the selected anode spot being selected from an array of anode spots on the anode surface;

focusing means receptive of the x-rays from the selected anode spot for focusing a predetermined energy band of the x-rays as an x-ray spot on a selected pixel area of the specimen surface, such that photoelectrons are emitted from the selected pixel area, the selected pixel area corresponding to the selected anode spot and thereby being selected from an array of pixel areas corresponding to the array of anode spots;

detection means receptive of the photoelectrons from the selected pixel area for producing signals representative of the photoelectrons; and display means receptive of the representative signals for displaying specimen information associated with the photoelectrons;

wherein the focusing means comprises a base member having a polished face with a concave curvature and a monochromator crystal arrangement comprising a plurality of crystal platelets having an uniform thickness and being formed of common material, lattice structure, and crystalline orientation, the crystal platelets having a polished side bonded to the polished face juxtaposed in crystalline alignment so as to assume the concave curvature and form the monochromator.

2. The instrument of claim 1 wherein the photoelectrons have electron energies characteristic of chemical species in the selected pixel area, and the detection means comprises analyzer means receptive of the photoelectrons for analyzing the electron energies thereof, such that the specimen information is representative of the electron energies and thereby the chemical species in the selected pixel area.

3. The instrument of claim 2 wherein the analyzer means comprises deflector means to deflect the photoelectrons in a predetermined path for selective detection according to a selected electron energy, and signal means for applying to the deflector a selected electrical signal determinative of the path and thereby the selected energy.

4. The instrument of claim 2 wherein the monochromator is disposed cooperatively with the anode surface and the specimen surface so as to effect the x-ray spot in the predetermined energy band as an x-ray image of the anode spot.

5. The instrument of claim 4 wherein the monochromator, the anode surface and the specimen surface are cooperatively positioned on a Rowland circle to effect the x-ray image.

6. The instrument of claim 1 wherein the platelet from an initial array of juxtaposed sections delineated on a flat surface of a single crystal member, the sections being cut from the crystal member to form the platelets, the polished side of the platelets being bonded to the polished face of the base member in a positioned array identical to that of the initial array, such that the platelets form a precision monochromator.

7. The instrument of claim 6 wherein the crystal platelets have an uniform thickness between 10 and 100 microns, and each side dimension of the platelets is between 10 and 50 mm.

8. The instrument of claim 6 wherein the platelets are formed of quartz with a crystal orientation of 100 relative to the face.

9. An instrument for analysis of a specimen surface, comprising:

an electron gun for producing a focused electron beam;

an anode with an anode surface disposed to receive the focused electron beam so as to generate x-rays;

rastering means for rastering the focused beam over an array of anode spots on the anode surface whereby the x-rays are generated sequentially from each of the anode spots;

focusing means receptive of the x-rays from the anode spots for focusing an energy band of the x-rays of predetermined energy as an x-ray spot on the specimen surface, the rastering effecting movement of the x-ray spot over an array of pixel areas on the specimen surface, such that photoelectrons are emitted sequentially from each pixel area with electron energies characteristic of chemical species in such each pixel area, the array of pixel areas corresponding to the array of anode spots;

analyzer means receptive of the photoelectrons from the sequential pixel areas for analyzing the electron energies;

display means cooperative with the analyzer means for displaying a mapping of specimen information representative of the electron energies and thereby the chemical species in the array of pixel areas; and a magnetic immersion lens disposed proximate the specimen surface with the specimen surface interposed between the immersion lens and the analyzer means, so that a magnetic field of the immersion lens collects a substantial portion of the photoelectrons from the specimen surface and directs the substantial portion to the analyzer means.

10. An instrument for analysis of a specimen surface, comprising:

an electron gun for producing a focused electron beam;

an anode with an anode surface disposed to receive the focused electron beam so as to generate x-rays;

rastering means for rastering the focused beam over an array of anode spots on the anode surface whereby the x-rays are generated sequentially from each of the anode spots;

focusing means receptive of the x-rays from the anode spots for focusing an energy band of the x-rays of predetermined energy as an x-ray spot on the specimen surface, the rastering effecting movement of the x-ray spot over an array of pixel areas on the specimen surface, such that photoelectrons are emitted sequentially from each pixel area with electron energies characteristic of chemical species in such each pixel area, the array of pixel areas corresponding to the array of anode spots;

analyzer means receptive of the photoelectrons from the sequential pixel areas for analyzing the electron energies; and display means cooperative with the analyzer means for displaying a mapping of specimen information representative of the electron energies and thereby the chemical species in the array of pixel areas;

wherein the focusing means comprises a base member having a polished face with a concave curvature and a monochromator crystal arrangement comprising a plurality of crystal platelets having an uniform thickness and being formed of common material, lattice structure, and crystalline orientation, the crystal platelets having a polished side bonded to the polished face juxtaposed in crystalline alignment so as to assume the concave curvature and form the monochromator.

11. The instrument of claim 10 wherein the monochromator is disposed cooperatively with the anode surface and the specimen surface so as to effect the x-rays spot in the predetermined energy band as an x-ray image of the anode spot.

12. The instrument of claim 11 wherein the monochromator, the anode surface and the specimen surface are cooperatively positioned on a Rowland circle to effect the x-ray image.

13. The instrument of claim 10 wherein the platelets originate from an initial array of juxtaposed sections delineated on a flat surface of a single crystal member, the sections being cut from the crystal member to form the platelets, the polished side of the platelets being bonded to the polished face of the base member in a positioned array identical to that of the initial array, such that the platelets form a precision monochromator.

14. The instrument of claim 13 wherein the platelets have an uniform thickness between 10 and 100 microns, and each side dimension of the platelets is between 10 and 50 mm.

15. The instrument of claim 13 wherein the platelets are formed of quartz with a crystal orientation of 100 relative to the face.

16. An instrument for analysis of a specimen surface, comprising:
an electron gun for producing a focused electron beam;
an anode with an anode surface disposed to receive the focused electron beam so as to generate x-rays;
rastering means for rastering the focused beam over an array of anode spots on the anode surface such that the x-rays are generated sequentially from each of the anode spots;
focusing means receptive of the x-rays from the anode spots for focusing an energy band of the x-rays of predetermined energy as an x-ray spot on the specimen surface, the rastering effecting movement of the x-ray spot sequentially over each pixel area in an array of pixel areas on the specimen surface, such that photoelectrons are emitted from each pixel area with electron energies characteristic of chemical species in such pixel area, the array of pixel areas corresponding to the array of anode spots;
detector means receptive of the photoelectrons for generating corresponding photoelectron signals; and processing means receptive of the photoelectron signals and cooperative with the rastering means means so as to produce a scanning photoelectron image of the specimen surface;
wherein the focusing means comprises a base member having a polished face with a concave curvature and a monochromator crystal arrangement comprising a plurality of crystal platelets having an uniform thickness and being formed of common material, lattice structure and crystalline orientation, the crystal platelets having a polished side bonded to the polished face juxtaposed in crystalline alignment so as to assume the concave curvature and form the monochromator.

17. The instrument of claim 16 wherein the monochromator is disposed cooperatively with the anode surface and the specimen surface so as to effect the x-ray spot in the predetermined energy band as an x-ray image of the anode spot.

18. The instrument of claim 17 wherein the monochromator, the anode surface and the specimen surface are cooperatively positioned on a Rowland circle to effect the x-ray image.

19. The instrument of claim 16 wherein the platelets originate from an initial array of juxtaposed sections delineated on a flat surface of a single crystal member, the sections being cut from the crystal member to form the platelets, the polished side of the platelets being bonded to the polished face of the base member in a positioned array identical to that of the initial array, such that the platelets form a precision monochromator.

20. The instrument of claim 19 wherein the platelets have an uniform thickness between 10 and 100 microns, and each side dimension of the platelets is between 10 and 50 mm.

21. The instrument of claim 19 wherein the platelets are formed of quartz with a crystal orientation of 100 relative to the face.

22. An instrument for analysis of a specimen surface, comprising:
an electron gun for producing a focused electron beam;
an anode with an anode surface disposed to receive the focused electron beam so as to generate x-rays;
rastering means for rastering the focused beam over an array of anode spots on the anode surface such that the x-rays are generated sequentially from each of the anode spots;
focusing means receptive of the x-rays from the anode spots for focusing an energy band of the x-rays of predetermined energy as an x-ray spot on the specimen surface, the rastering effecting movement of the x-ray spot sequentially over each pixel area in an array of pixel areas on the specimen surface, such that photoelectrons are emitted from each pixel area with electron energies characteristic of chemical species in such pixel area, the array of pixel areas corresponding to the array of anode spots;
detector means receptive of the photoelectrons for generating corresponding photoelectron signals;
processing means receptive of the photoelectron signals and cooperative with the rastering means means so as to produce a scanning photoelectron image of the specimen surface; and
a magnetic immersion lens disposed proximate the specimen surface with the specimen surface interposed between the immersion lens and the analyzer means, so that a magnetic field of the immersion lens collects a substantial portion of the photoelectrons from the specimen surface and directs the substantial portion to the analyzer means.

23. An article including a precision concave monochromator for focussing a selected band of x-rays, comprising a base plate having a polished face with a concave curvature and a monochromator crystal arrangement comprising a plurality of crystal platelets having an uniform thickness, wherein the platelets originate from an initial array of juxtaposed sections delineated on a flat surface of a single crystal member, the sections being cut from the crystal member to form the platelets, a polished side of the platelets being bonded to the polished face of the base plate in a positioned array identical to that of the initial array, such that the platelets form the precision monochromator.

24. The article of claim 23 wherein the crystal platelets have an uniform thickness between 10 and 100 microns, and each side dimension of the platelets is between 10 and 50 mm.

25. The article of claim 23 wherein the platelets are formed of quartz with a crystal orientation of 100 relative to the face.

26. The article of claim 23 wherein the base plate is formed of the same material as that of the platelets.

27. A method of producing a precision concave monochromator for focussing a selected band of x-rays, comprising the steps of: forming a polished face having a concave curvature on a base member, delineating an initial array of juxtaposed sections on a flat surface of a single crystal member, cutting the delineated sections in an uniform thickness from the crystal member to form a plurality of platelets, polishing a side of each platelet, bonding the polished side of the platelets to the polished face of the base member so as to assume the concave curvature, and juxtapossing the platelets on the polished face of the base member in crystalline alignment in a positioned array identical to that of the initial array, such that the aligned platelets form the precision concave monochromator.

28. The method of claim 27 wherein the step of polishing is effected prior to the step of cutting.

29. The method of claim 27 further comprising the steps of, in sequence commencing prior to the step of cutting, initially polishing an optical flat to the flat surface of the single crystal member, effecting the step of delineating, effecting the step of cutting by cutting rigidly thick platelets from the crystal member, mounting the thick platelets on an optically flat support member such that the thick platelets are juxtaposed on the support member in crystalline alignment in an array identical to that of the initial array with an exposed side, thinning the mounted platelets on the exposed side to a predetermined thickness, polishing the exposed thinned side to the optical flat parallel to the flat surface, and removing the platelets from the support member for bonding of the exposed polished side to the polished face of the base member.

30. An instrument for x-ray photoelectron analysis of a specimen surface, which comprises a precision monochromator article for focussing a selected band of x-rays onto the specimen surface t o effect photoelectrons therefrom, the article comprising a base plate having a polished face with a concave curvature and a monochromator crystal arrangement comprising a plurality of crystal platelets having an uniform thickness, wherein the platelets originate from an initial array of juxtaposed sections delineated on a flat surface of a single crystal member, the sections being cut from the crystal member to form the platelets, a polished side of the platelets being bonded to the polished face of the base plate in a positioned array identical to that of the initial array, such that the platelets form a precision concave monochromator.

31. The instrument of claim 30 wherein the crystal platelets having an uniform thickness between 10 and 100 microns, and each side dimension of the platelets is between 10 and 50 mm.

32. The instrument of claim 30 wherein the platelets are formed of quartz with a crystal orientation of 100 relative to the face.

33. The instrument of claim 30 wherein the base plate is formed of the same material as that of the platelets.

34. The instrument of claim 30, wherein the instrument comprises analyzer means receptive of the photoelectrons from sequential pixel areas on the specimen surface for analyzing electron energies, and a magnetic immersion lens disposed proximate the specimen surface with the specimen surface interposed between the immersion lens and t he analyzer means, so that a magnetic field of the immersion lens collects a substantial portion of the photoelectrons from the specimen surface and directs the substantial portion to the analyzer means.

* * * * *